(12) United States Patent
Alberto et al.

(10) Patent No.: US 7,692,002 B2
(45) Date of Patent: Apr. 6, 2010

(54) METAL COMPLEXES HAVING VITAMIN $B_{12}$ AS A LIGAND

(75) Inventors: Roger Alberto, Winterthur (CH); Susanne Barbara Kunze, Adlikon (CH); Hector Knight Castro, Alkmaar (NL); Stefan Mundwiler, Aarau (CH)

(73) Assignee: University of Zurich, Zurich (CH)

( * ) Notice: Subject to any disclaimer, the term of this patent is extended or adjusted under 35 U.S.C. 154(b) by 941 days.

(21) Appl. No.: 10/585,294

(22) PCT Filed: Jan. 10, 2005

(86) PCT No.: PCT/EP2005/000168
§ 371 (c)(1), (2), (4) Date: Jul. 6, 2006

(87) PCT Pub. No.: WO2005/068483
PCT Pub. Date: Jul. 28, 2005

(65) Prior Publication Data
US 2009/0175775 A1 Jul. 9, 2009

(30) Foreign Application Priority Data
Jan. 8, 2004 (EP) .................. 04075003
Oct. 25, 2004 (EP) .................. 04077937

(51) Int. Cl.
*C07D 487/22* (2006.01)
*C07F 15/00* (2006.01)
*C07F 7/22* (2006.01)
*C07H 23/00* (2006.01)

(52) U.S. Cl. .................. 540/145; 556/28; 556/137; 536/26.44; 514/492; 424/9.42

(58) Field of Classification Search .................. 556/28, 556/137; 536/26.44; 540/145; 514/492; 424/9.42
See application file for complete search history.

(56) References Cited

U.S. PATENT DOCUMENTS

| | | | |
|---|---|---|---|
| 4,560,782 A | 12/1985 | Papageorgiou et al. | |
| 5,393,909 A * | 2/1995 | Khokhar et al. | ............. 556/137 |
| 6,180,085 B1 | 1/2001 | Achilefu et al. | |
| 6,316,675 B1 | 11/2001 | Reetz et al. | |
| 6,641,798 B2 | 11/2003 | Achilefu et al. | |
| 6,844,425 B1 * | 1/2005 | Alberto et al. | ............. 530/391.1 |
| 7,582,295 B2 * | 9/2009 | Alberto et al. | ............. 424/130.1 |
| 2004/0224921 A1 | 11/2004 | Grissom et al. | |

OTHER PUBLICATIONS

Schibli et al., Bioconjugate Chemistry, vol. 11, No. 3, pp. 345-351 (2000).*
Sheldrick, Phase Annealing in *SHELX*-90: Direct Methods for Larger Structures, Acta Cryst., 1990, A46, pp. 467-473.

b1(a)

b1(b)

b2(a)

b2(b)

b3(a)

b3(b)

b4(a)

b4(b)

b5 b6 b7

Altomare et al., *SIR*97: a new tool for crystal structure determination and refinement, J. Appl. Cryst., 1999, 32, pp. 115-119.

Alberto et al., Synthesis and Reactivity of [Net$_4$]$_2$[ReBr$_3$(CO)$_3$]. Formation and Structural Characterization of the . . . , J. Chem.. Soc, Dalton Trans. 1994, pp. 2815-2820.

Alberto et al., Synthesis and Properties of Boranocarbonate: A Convenient in Situ . . . , J. Am. Chem. Soc., 2001, 123, pp. 3135-3136.

Kunze et al., Vitamin B12 as a Ligand for Technetium and Rhenium Complexes**, Angew. Chem. Int. Ed., 2004, 43, pp. 5025-5029 XP-002328039.

\* cited by examiner

*Primary Examiner*—Porfirio Nazario Gonzalez

(57) ABSTRACT

The present invention relates to a metal complex of the general formula M(L)$_n$, wherein each L is independently selected and represents a ligand and at least one L is vitamin B$_{12}$ (cyanocobalamin) or a derivative thereof bound through the nitrogen atom of its cyanide group to M, which is an element selected from the transition metals, thus, forming a M-NC-[Co] moiety with [Co] representing vitamin B$_{12}$ without cyanide and wherein n is 1, 2, 3, 4, 5 or 6. The complex can be prepared by mixing a precursor molecule with vitamin B$_{12}$. The metal complexes can be used for radiodiagnostics, chemotherapy and radionuclide therapy.

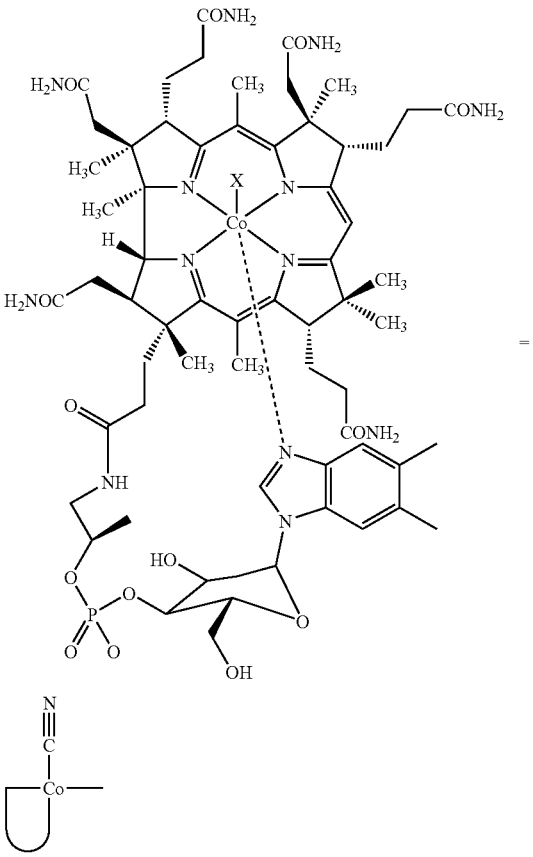

23 Claims, 6 Drawing Sheets

Vitamine B12 labeling met Carbonyl.
Detector: NaI kristal
Flow: 0,5 ml/min.
Scheidingskolom: Macherey-Nagel Nucleosil C18
Mobiele fase: A: 0,1% TFA and B:100% McOH
Looptijd: 40 min.
Kolom temperatuur: 25C
Opstelling: 4
D:\R&D\ervries\Methods\VB12_Carbonyl_Labeling.met
D:\R&D\ervries\Data\04335ervries4_091204_004
Isolink batch: 167552 labeled with 1 ml pertechenate and boiled for 20 min. Brought at pH 3. From this solution 0,1 ml + 0,9 ml Vitamine B12 solution 10 mM and boiled for 30 min.

Fourth Labeling

Detector D

| Pk # | Retention Time | Start Time | Stop Time | Area | Area Percent | Theoretical plates | Asymmetry | Resolution |
|---|---|---|---|---|---|---|---|---|
|  | 4.933 |  |  | 42352 | 0.15 | 0.00 | 0.00 | 0.00 |
| 2 | 20.267 |  |  | 21132 | 0.07 | 0.00 | 0.00 | 0.00 |
| 3 | 22.017 |  |  | 196144 | 0.69 | 0.00 | 0.00 | 0.00 |
| 4 | 24.317 |  |  | 28070230 | 99.08 | 0.00 | 0.00 | 0.00 |

| Totals |  |  |  | 28329858 | 100.00 |  |  |  |

Fig. 4

Fig. 5A compound b1 compound b4

Fig. 5B compound b5

METAL COMPLEXES HAVING VITAMIN B$_{12}$ AS A LIGAND

FIELD OF THE INVENTION

The invention relates to metal complexes that contain vitamin B$_{12}$ as a ligand. The invention further relates to the use of these complexes in radiodiagnostics, radionuclide therapy, chemotherapy or as catalysts.

BACKGROUND ART

The current anti-cancer drugs, such as cisplatin, are also toxic to normal, healthy cells. The relatively high doses that need to be administered to a patient cause severe side effects. Enhanced selectivity by targeting cancer cells would be beneficial for the therapeutic index and the life quality of the patient.

In radionuclide therapy use is made of the metabolic accumulation of a radiopharmaceutical to deliver a therapeutic radiation dose to a tissue. The critical factor for successful radionuclide therapy is target tissue accumulation in relation to normal tissue, which is in the range of 5 to 100 in all methods known so far. An exception to this is the very successful iodine metabolic therapy of thyroid disease. Due to the low ratio of accumulation in target to normal tissue the radiation burden to the patient's normal tissues is often relatively high. A need thus exists for a way to specifically deliver the radionuclide to the target tissue.

An interesting candidate compound that may lead to site specific uptake is vitamin B$_{12}$. Fast proliferating cancer cells are so-called high B$_{12}$ consumers. This very high demand makes vitamin B$_{12}$ a potential "trojan horse" for delivering therapeutic agents.

Cyanocobalamin (vitamin B$_{12}$) is well known and its chemistry has been comprehensively reviewed. Many patents and publications exist for the derivatization of vitamin B$_{12}$ at the cobalt, corrin ring or the ribose moiety. Some of these vitamin B$_{12}$ derivatives have been proposed for application in cancer therapy or diagnosis but none have entered the market yet.

US2004/224921 for example relates to fluorescent cobalamins comprised of a fluorescent, phosphorescent, luminescent or light-producing compound that is covalently linked to cobalamin. These fluorescent cobalamins can be used as diagnostic and prognostic markers to distinguish cancer cells and tissues from healthy cells and tissues, and to determine if an individual will respond positively to chemotherapy using cobalamin-based therapeutic bioconjugates. The fluorescent, phosphorescent or light-producing compounds can be covalently linked to the cobalt atom, the corrin ring, or the ribose moiety of cobalamin. This type of derivatization is also described for non-fluorescent compounds.

Derivatization directly at the cobalt leads to a compound that retains more than 90% of the vitamin B$_{12}$ activity. Derivatization at that position is thus an obvious choice. However, these compounds have also disadvantages. For example, cobalt alkylated compounds are light sensitive.

Derivatizations at the ribose or at positions on the corrin framework have the drawback of not being cleavable, thus influencing the biological behaviour of vitamin B$_{12}$ significantly.

A need therefore exists for a drug which can be used for the diagnosis and treatment of cancer, which does not carry severe side effects nor leads to a high radiation burden.

SUMMARY OF THE INVENTION

It was found according to the invention that certain metal complexes are able to coordinate directly to the cyanide group in vitamin B$_{12}$. It could be shown that this type of binding is occurring in particular for the complex [Tc(N∩O)(OH$_2$)(CO)$_3$] (N∩O=bidentate ligand) in which the nitrogen atom of cyanide binds directly to the Tc metal centre forming a [Co]-CN—Tc moiety. This represents the prototypical example for a complex in which vitamin B$_{12}$ acts as a ligand for a metal, in this case for Tc. However, other metal complexes in which vitamin B$_{12}$ is a ligand that is linked to the metal through its cyanide are also part of this invention. In all these metal complexes vitamin B$_{12}$ is acting as a ligand.

The invention for the first time proposes to coordinate vitamin B$_{12}$ through its cyanide to a metal to form a [Co]-CN-M complex, wherein [Co] represents vitamin B$_{12}$ without cyanide. The inventors have found that such vitamin B$_{12}$ derivatives are chemically stable and can be easily produced.

With the exception of the CN position, all other sites in vitamin B$_{12}$ have been proposed in the literature for labelling. The cyanide was not used before since it was not expected to act as a ligand group.

The invention thus relates to metal complexes of the general formula M(L)$_n$, wherein each L is independently selected nd is a ligand and at least one L is selected from vitamin B$_{12}$ (cyanocobalamin) and its derivatives bound through the nitrogen atom of its cyanide group to M, which is an element selected from the transition metals, thus, forming a M-NC-[Co] moiety wherein [Co] represents vitamin B$_{12}$ or its derivative without cyanide and wherein n is 1, 2, 3, 4, 5 to 6.

The different ligands L within one metal complex need not be the same but each L can be independently selected.

M can be a transition metal such as selected from technetium, ruthenium, rhodium, rhenium, palladium, platinum, iridium and copper.

For applications in cancer diagnosis and/or therapy, the metal is advantageously a radioisotope of Re or Tc, such as selected from $^{99m}$Tc, $^{188}$Re, $^{186}$Re, $^{105}$Rh.

When M is technetium or rhenium, the other ligands L are suitably three carbonyl groups (CO's) and optionally a bidentate ligand, optionally coupled to another metal, a biologically active molecule or another molecule, such as a fluorescent agent. It is also possible to have two monodentate ligands like H$_2$O or Cl instead of one bidentate ligand. Other monodentate ligands are monocarboxylate derivatives, mono thiolate derivatives, aliphatic/aromatic amines etc, optionally substituted with a biologically active molecule.

The bidentate ligand is suitably selected from two aliphatic and/or aromatic amine parts or one aliphatic or aromatic amine part and an anionic group such as a carboxylate, a thiolate or a hydroxylate. Examples are α-amino acids or derivatives of picolinic acid.

The ligand L may also be a biologically active molecule.

When M is platinum, L is selected from a ligand containing N, S, P O, C as the metal binding atom or any other donor with one non-binding electron pair available for coordination to the metal, optionally coupled to a biologically active molecule.

The biologically active molecule or other molecule is selected from fluorescing agents, pharmacophores with cytotoxic, cytostatic or other pharmacological activities, optical dyes, NIR dyes or phosphorescent dyes (such as disclosed in U.S. Pat. No. 6,180,085 and U.S. Pat. No. 6,641,798). Fluorescing agents are for example fluoresceine, pyrene, acridine, dansyl or others. These can be used for diagnostic and prognostic purposes. Cytotoxic or cytostatic agents are for example tamoxifen, methotrexate and cyclophosphamid or other compounds with known pharmacological activity (for therapy). Alternatively, the other molecule may be a radioactive compound for diagnostic or therapeutic purposes. The biologically active molecule may also be a nucleic acid, such as RNA or DNA, in particular antisense RNA or DNA.

The invention relates further to a process for preparing these metal complexes containing vitamin $B_{12}$ or a derivative thereof as a ligand, comprising mixing of vitamin $B_{12}$ with a precursor complex, wherein M is a transition metal, n is 2, 3, 4, 5 or 6 and L is a ligand to obtain a metal complex with a stable [Co]-CN-M bridge. The precursor complex has the general formula $M(L)_{n-1}L'$, wherein L' is a ligand that is substituted by the vitamin $B_{12}$. The transition metal is suitably selected from technetium, ruthenium, rhodium, rhenium, palladium, platinum, iridium and copper.

The invention further relates to a precursor complex having the general formula $M(L)_{n-1}$, wherein M is a transition metal, preferably selected from technetium, ruthenium, rhodium, rhenium, palladium, platinum, iridium and copper, n is 2, 3, 4, 5 or 6 and L is a ligand.

The invention also relates to the metal complexes of the invention for use as a diagnostic or therapeutic agent, and to pharmaceutical compositions comprising the metal complexes of the invention.

Furthermore, the invention relates to metal complexes of the invention, wherein M is a metal with catalytic activity, such as ruthenium, palladium, iridium, platinum or rhodium.

DETAILED DESCRIPTION OF THE INVENTION

The invention thus relates to metal complexes that contain vitamin $B_{12}$ or one of its derivatives as a ligand. In one embodiment, the metal can be a radionuclide, such as $^{99m}$Tc or $^{188}$Re, for radiopharmaceutical application in e.g. cancer diagnosis and radionuclide therapy. In another embodiment, metal complexes obtained through coupling of other metal fragments (e.g. Rh, Pt, Pd) to vitamin $B_{12}$ through the cyanide can be used for chemotherapy or stereospecific and/or enantioselective catalysis.

The reaction of vitamin $B_{12}$ with metal complexes in a $d^3$, $d^6$ or $d^8$ electronic configuration leads to the formation of a stable [Co]-CN-M bridge. If M is $^{99m}$Tc, this is a convenient method of labelling vitamin $B_{12}$. If M is e.g. Rh(I) the corresponding complex can be used for catalysis since vitamin $B_{12}$ provides a stereospecific environment.

If M is $^{99m}$Tc or $^{188}$Re, then the precursor complex is suitably (Tc(N∩O)(OH$_2$)(CO)$_3$) in which OH$_2$ is substituted by [Co]-CN. The ligand N∩O (or other donor combinations) is variable. In the absence of other ligands (mono- or bidentate), only vitamin $B_{12}$ is coordinated to the metal. In the absence of a bidentate N∩O ligand or a bidentate ligand of any other donor combination, one water is replaced by vitamin $B_{12}$ and the two remaining positions at Tc remain occupied by H$_2$O or Cl. In solution, the complexes b1-b4 with $^{99m}$Tc and Re are received in quantitative yield although the isolated yield as a solid for Re was lower (see experimental part).

The ligand N∩O (or others) can also be bifunctional. One of the functions is used for coordination to the metal and the second function can additionally be coupled to e.g. a targeting vector. This enables combination of receptor targeting, internalization and trapping of labelled vitamin $B_{12}$. Such a derivative is also called a "trojan horse" if the additional functionality is e.g. enzymatically cleaved inside the cell. It releases then a functionally active or inactive vitamin $B_{12}$ compound.

Examples of bifunctional ligands are 1,4-dipicolinic acid, 1,5-dipicolinic acid, 1,2-imidazole dicarboxylic acid, 1,2-piperazine dicarboxylic acid, amino acids, like glutamic acid, lysine.

The structural and functional variability of the different complexes that can be attached to the cyanide of vitamin $B_{12}$ thus offers the possibility to finetune and improve the general behaviour and bio-distribution of the [Co]-CN-M $(L)_{n-1}$, complex.

Vitamin $B_{12}$ as a ligand exhibits unexpected stability in the complexes of the invention. It coordinates as native vitamin $B_{12}$. If it is released from the metal complexes of the invention by substitution with another ligand, it is released as native vitamin $B_{12}$ and is, thus, not harmful to the body and safe.

When vitamin $B_{12}$ coordinates to a toxic compound, its toxicity is expected to be reduced. It is known in the literature that certain enzymes such as adenosyl transferase cleave the cyanide or any other group attached to the cobalt in vitamin $B_{12}$ from [Co]-CN. This means that also the metal complex $M(L)_{n-1}$ is cleaved and released from vitamin $B_{12}$. Upon release of the toxic moiety, which can be the metal complex or a molecule attached to the metal complex, in a cancer cell that has taken up the vitamin $B_{12}$ complex the toxic moiety can perform its mode of action without inducing harmful side effects in non-targeted cells.

It was furthermore established that the kind of coupling via the cyanide as suggested by the invention does not affect binding of the vitamin $B_{12}$ to transcobalamin I (TCI), transcobalamin II (TCII) and intrinsic factor (TF). It is thus still taken up by the cell and can thus successfully be used as a trojan horse.

The coupling of any other ligand L to M is via a binding atom selected from S, N, C, O, P or another atom containing one non-binding electron pair. The binding atom is thus part of a bigger moiety L.

The synthesis of the metal complexes of the invention is simple because there is no need of derivatization of the $B_{12}$ framework. The products are readily available in very high yields. When a derivative of vitamin $B_{12}$ is used as the ligand, derivatization of vitamin $B_{12}$ can be performed before synthesis of the metal complex.

Figure 1:
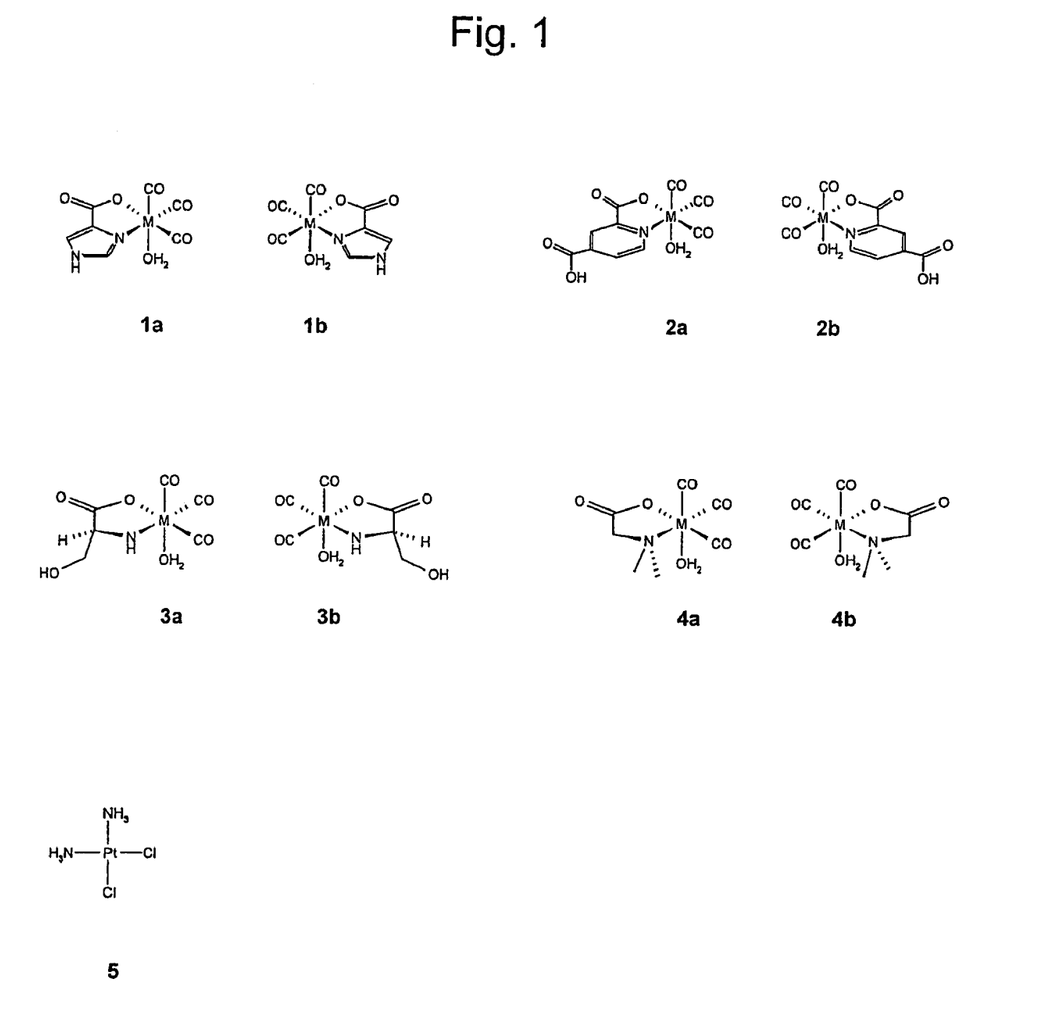
FIG. 1 shows precursor complexes before coupling to vitamin $B_{12}$. The numbering corresponds to the numbering used in the Examples.
Figure 2:
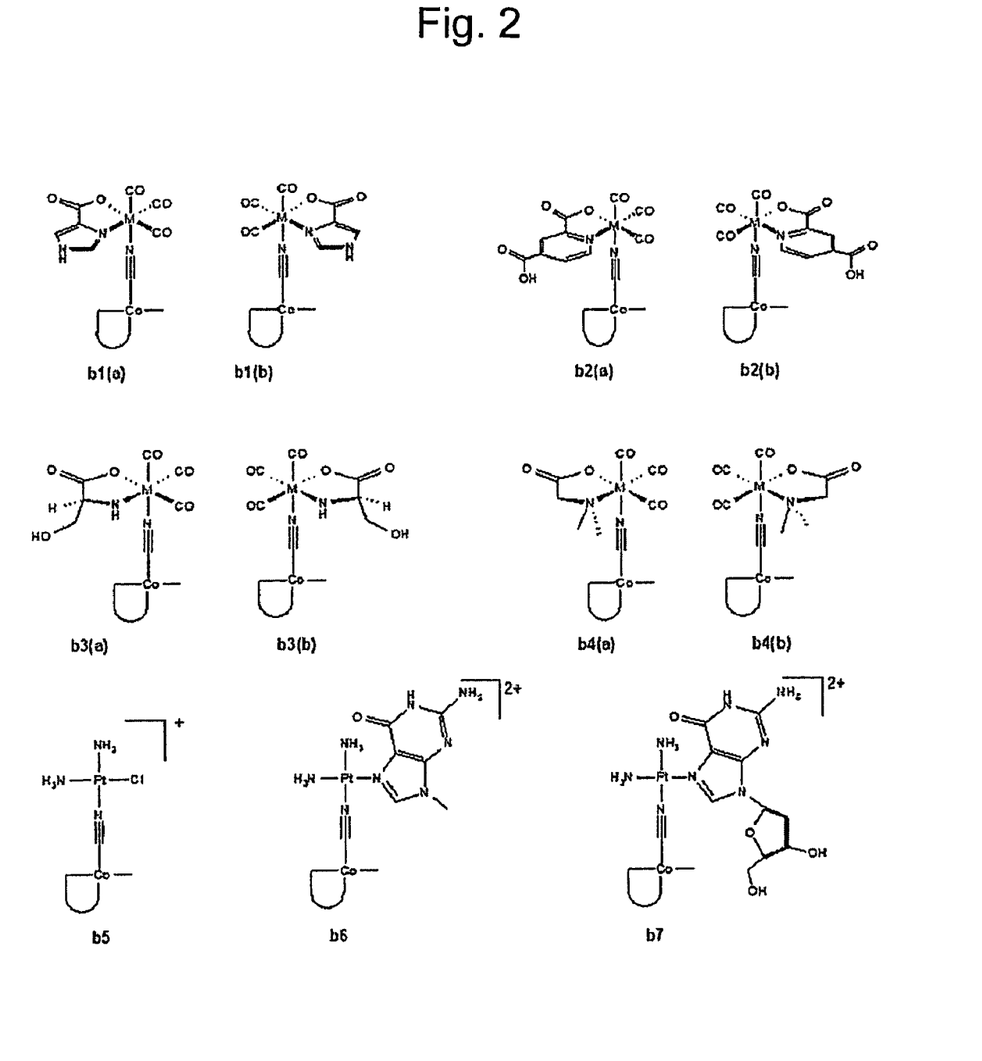
FIG. 2 shows examples of metal complexes of the invention. The numbering corresponds to the numbering used in the Examples.

The compounds depicted in FIGS. 1 and 2 are compounds of the invention.

To obtain the products b1-b4, the complex [M(OH$_2$)(L$^2$)(CO)$_3$] (M=$^{185,187}$Re, $^{99m}$Tc) was coordinated to vitamin $B_{12}$. The complex [M(OH$_2$)(L$^2$)(CO)$_3$] is synthesized prior to the introduction of $B_{12}$ reacting the fac-[$^{99m}$Tc(OH$_2$)$_3$(CO)$_3$]$^+$ complex, respectively the [ReBr$_3$(CO)$_3$]$^{2-}$ complex, with a bidentate ligand L$^2$. This is the so-called mixed ligand [2+1]-approach. The bridging metal can be considered as a mediator between vitamin $B_{12}$ and the ligand L$^2$, whereas the ligand L$^2$ is variable.

The diastereomers (a) and (b) of b1-b4 can be separated from each other. The pure diastereomers are kinetically stable and interconvert, if ever, only slowly into each other. The distinct difference in HPLC retention time of the diastereoisomers indicates the possibility of using vitamin $B_{12}$ as a chiral ligand for introducing enantio-selectivity or diastereoselectivity in reactions using metal complexes as catalysts.

In the metal complexes of the invention, vitamin $B_{12}$ is not replaced by competing ligands, such as e.g. chloride, acetonitrile, water or other naturally occurring ligand groups.

Since light sensitivity in coenzyme $B_{12}$ compounds containing Co—C (C≡alkyl) bond is related to the break of the Co—C bond, the complexes of the invention are not light sensitive at all. This is an important advantage as it simplifies storage and handling.

For use in diagnosis or radionuclide therapy, the subject metal complexes can be administered to the host, mostly a mammalian host, normally by injection, intravenously, intraarterially, peritoneally, intratumorally, or orally by means of a dosage form that will release the metal complex in the stomach. The route of administration depends upon the particular site at which the radionuclide is desired. Generally, from about 0.1 to 2 ml will be injected into a host, depending upon the weight of the host. Usually the treatment regime is tailor made because it depends on weight, type of tumor, age etc of the patient to be treated. The skilled person in the field is capable of determining the necessary radioactive dose. After administration of the radionuclide, depending upon its purpose, the host may be treated in various ways for diagnosis or therapy by detecting the radioactive emissions from the site or sites where the radionuclide specifically binds.

When the metal complexes are platinum complexes, they can be used in a pharmaceutical composition for chemotherapy. The route of administration is usually intravenous. Here again, the amount of metal complex that needs to be administered is determined for each patient separately.

The compound b1 represents a typical example of a $^{99m}$Tc derivative of vitamin $B_{12}$. It shows binding to the specific vitamin $B_{12}$ transport proteins.

Compound b2 is less lipohilic due to an additional carboxylic group in $L^2$ that is not involved in coordination to the $M(CO)_3$-moiety. The free carboxylic group can be considered as an anchor where any other biomolecule (e.g. peptide) or bioactive molecule or fluorescent marker can be attached to.

Compounds b3 and b4, although obtained in lower yields (~30%), demonstrate the possibility to combine any type of artificial or natural α-amino acid with vitamin $B_{12}$ via the [2+1]-approach.

Cytotoxicity tests of b4 with a mouse melanoma cell line (B16F1) showed 17% of proliferation inhibition at a concentration of 100 μM. At the same concentration, native cobalamin (vitamin $B_{12}$) showed no effect at all.

The cisplatinum compounds b5-b7 demonstrate the possibility that vitamin $B_{12}$ can also act as a ligand for metals different from Tc and Re. The chloride of complex b5 is labile and can be replaced by a more stable ligand like e.g. methylguanine b6 or guanosine b7. This offers the possibility to apply vitamin $B_{12}$ as a trojan horse to deliver antisense RNA or DNA sequences into the cells and the cell nucleus for transcription or translation silencing.

Cytotoxicity tests with a mouse melanoma cell line (B16F1) showed a percentage of proliferative cells of 20% in case of b5, and 30% in case of b6.

The present invention is illustrated in the Examples by reference to compounds in which the ligands form either a technetium or rhenium tricarbonyl, in which one of the $OH_2$ moieties is replaced by vitamin $B_{12}$ and that may be further derivatized at the remaining $OH_2$ moieties, or a platinum compound, such as cisplatin, in which one of the chloro atoms is replaced with vitamin $B_{12}$ and the other chloro atom is optionally any other molecule.

However, the basic inventive idea is using the cyanide on vitamin $B_{12}$ for derivatization. Based on this idea the skilled person is very well capable of defining other derivatives that are not as such disclosed herein but that still use the inventive idea. Such compounds are also part of this invention.

The invention is further illustrated in the non-limiting examples that follow, in which reference is made to the following figures.

EXAMPLES

Materials And Methods

All chemicals were purchased at highest commercial quality from Merck, Dietikon (CH), Aldrich or Fluka, Buchs (CH) and were used without further purification, unless stated otherwise.

All reactions were performed under nitrogen or argon atmosphere. Reactions were monitored by HPLC.

HPLC analyses were performed on a Merck-Hitachi L-7000 system equipped with a diode array UV/Vis detector and a EG&G Berthold LB 508 radiometric detector. Macherey Nagel Nucleosil C-18ec RP columns (5 μm particle size, 100 Å pore size, 250×3 mm) and Merck C-18e RP Supersphere® columns (100 Å pore size, 250×4 mm) and Waters XTerra RP8 columns (5 μm particle size, 3.0×100 mm) were used for separation. Different HPLC solvent systems and gradients were used: Solvent system 1: 0.1% AcOH and 10% $CH_3CN$ in water, pH 3 (A) and methanol (B). Solvent system 2: 0.1% Triethylammonium acetate and 10% $CH_3CN$ in water, pH 8 Solvent system 3: Trifluoroacetic acid, 0.1% in water (A) and methanol (B). Gradient 1: 0-3 min. 100% A, 3.1-9 min. 75% A, 9.1-20 min. 66%→0% A, 20-25 min. 0% A; 0.5 ml/min., or as mentioned. Gradient 2: 0-40 min. 100%→0% A, 30.1-40 min. 0% A, 40.1-42 min. 0%→100% A, 42-50 min. 100% A. Gradient 3: 0-5 min. 100% A, 5.1-40 min. 100%→65% A, 40.1-45 min. 0% A, 45.1-53 min. 100% A. Gradient 4: 0-5 min. 0%→20% B, 5-45 min. 20%.→65% B. Gradient 5: 0-10 min. 20% B, 10-30 min. 20%→40% B. Gradient 6: 0-30 min. 25%→65% B. Gradient 7: 0-5 min. 25% B, 5.1-30 min. 25%→100% B.

Preparative HPLC separations were performed on a Varian Prostar system equipped with two Prostar 215 pumps and a Prostar 320 UV/Vis detector, using Macherey Nagel Nucleosil C-18ec RP columns (7 μm particle size, 100 Å pore size, 250×20 mm, 10 ml/min. flow rate, and 250×40 mm, 40 ml/min. flow rate) and Waters XTerra Prep RP8 column (5 μm particle size, 100×30 mm, 30 ml/min. flow rate).

Electrospray ionization mass spectra (ESI-MS) were recorded on a Merck Hitachi M-8000 spectrometer.

UV/Vis spectra were recorded on a Varian Cary 50 spectrometer.

IR spectra were recorded on a Bio-Rad FTS-45 spectrometer with the samples in compressed KBr pills, unless mentioned differently.

RAMAN spectra were recorded on a Renishaw Ramanscope continuous wave instrument equipped with three lasers at 514 nm, 633 nm and 785 nm wavelength.

NMR spectra were recorded on a Varian Gemini 200 MHz or 300 MHz and a Bruker DRX 500 MHz spectrometer. The chemical shifts are reported relative to TMS using the residual solvent protons as internal standard. The chemical shifts of $^{31}$P NMR spectra are reported relative to orthophosphoric acid at 0 ppm. The chemical shifts of $^{14}$N NMR spectra are reported relative to nitromethane at 0 ppm. Peak assignments of cobalamin derivatives were determined by interpretation of the $^1$H COESY, the C—H correlation, the DEPT and (in some cases) the ROESY spectra.

MALDI-ToF mass spectra were measured on a Voyager-DE PRO with a-cyano-4-hydroxycinnamic acid as matrix. CV measurements were performed using a 757 VA Computrace Metrohm cyclo voltameter at room temperature using glassy carbon (Metrohm) as working electrode and auxiliary electrode, Ag/AgCl as reference electrode. The compounds were measured as a 1 mM solution in 0.1 M tetrabutylammonium hexafluorophosphate in methanol.

Crystallographic data were collected on a Stoe IPDS diffractometer at 183(2) K using graphite-monochromated Mo Kα radiation (λ=0.71073 Å). Suitable crystals were covered with Paratone N oil, mounted on top of a glass fibre and immediately transferred to a Stoe IPDS diffractometer. Data were collected at 183(2) K using graphite-monochromated Mo Kα radiation (λ=0.71073 Å). Eight thousand reflections distributed over the whole limiting sphere were selected by the program SELECT and used for unit cell parameter refinement with the program CELL[1]. Data was corrected for Lorentz and polarisation effects as well as for absorption (numerical). Structures were solved with direct methods using SHELXS-97[2] or SIR97[3] and were refined by full-matrix least-squares methods on F2 with SHELXL-97[4].

Elemental analyses were performed on a Leco CHNS-932 elemental analyser.

$[NEt_3]_2[ReBr_3(CO)_3]$[5] and fac-$[^{99m}Tc(OH_2)_3(CO)_3]^+$[6] were prepared as previously reported.

General Labelling Procedures

A 10 ml glass vial with rubber stopper was flushed with dinitrogen. 50 ml of a $10^{-3}$ M aqueous cobalamin derivative or ligand containing solution and 450 ml of a 0.1 M phosphate buffered $[^{99m}Tc(OH_2)_3(CO)_3]^+$ solution (pH 7.4) were added and the reaction mixture was kept at 75° C. for 30-45 minutes.

The cyanide bridged cobalamin derivatives were prepared as follows: 50 ml of a $10^{-3}$ M aqueous soln. of bidentate ligand and 450 ml of phosphate buffered $[^{99m}Tc(OH_2)_3(CO)_3]^+$ solution (pH 7.4) were added to a dinitrogen flushed vial (as described above) and the reaction mixture was kept at 90° C. for 30 minutes. 100 ml of this soln. were added to another vial, containing 100 ml of $10^{-2}$ M aq. vitamin $B_{12}$ solution. This reaction mixture was kept at 37° C. for 60 minutes.

HPLC analysis with γ-detection was performed to verify full conversion of the $^{99m}Tc$ species.

Synthesis of $[Re(imc)(OH_2)(CO)_3]$ (1)

$(NEt_4)_2[ReBr_3(CO)_3]$ (488 mg, 0.63 mmol) was dissolved in water (5 ml) and added to a solution of 4-imidazole carboxylic acid (imc) (71 mg, 0.63 mmol) in water (3 ml). After 2 h under reflux, the product precipitated as a white powder at r. t. Filtration, washing with diethyl ether and drying at high vacuum gave 186 mg of 1 (73%).

$^1$H NMR (300, DMSO-D6) δ 8.40 (s, 1H, imc), 7.68 (s, 1H, imc), 7.08 (br s, 1H, imc)

IR (KBr, cm$^{-1}$): 2039, 1936 $v_{C=O}$ (st)

MS (ESI+, MeOH) m/z: 764 (2M-2H$_2$O), 382 (M-H$_2$O)$^+$

Anal. Calcd for C$_7$H$_5$N$_2$O$_6$Re: C, 21.05; H, 1.26; N, 7.02. Found: C, 21.15; H, 1.41; N, 6.97.

Synthesis of $[Re(2,4-dipic)(OH_2)(CO)3]$ (2)

$(NEt_4)_2[ReBr_3(CO)_3]$ (101 mg, 0.13 mmol) was dissolved in water (10 ml). After addition of AgNO$_3$ (70 mg, 0.4 mmol) and stirring at r. t. for 3 h, AgBr was removed by filtration and pyridine-2,4-dicarboxylic acid (2,4-dipic) (24 mg, 0.13 mmol) was added to the colourless solution, followed by stirring at 50° C. for 2 h. The now yellow solution was cooled down and the product was allowed to crystallize at 4° C. for 12 h. The yellow crystals were collected by filtration, washed with water and dried at high vacuum to give the product in a yield of 38 mg (65%).

$^1$H NMR (300, DMSO-D6) δ 8.96 (d, 1H, pyridine), 8.34 (s, 1H, pyridine), 8.15 (d, 1H, pyridine), 7.50 (s, 1H, pyridine)

IR (KBr, cm$^{-1}$): 2036, 1920 $v_{C=O}$ (st)

MS (ESI+, MeOH) m/z: 438 (M-H$_2$O)$^+$

Anal. Calcd for C$_{10}$H$_6$NO$_8$Re: C, 26.45; H, 1.33; N, 3.07 Found: C, 26.15; H, 1.67; N, 3.07

Synthesis of $[^{99m}Tc(ser)(OH2)(CO)_3]$ (3)

Complex 3 was prepared according to the standard labelling procedure described in the chapter 'Materials and Methods'. Serine was labelled with a concentration of $10^{-3}$ M in the r.m. The $^{99m}Tc$ was completely converted after 40 min. at 90° C.

Synthesis of $[Re(dmg)(OH_2)(CO)_3]$ (4)

$(Et_4N)2[ReBr3(CO)3]$ (100 mg, 0.13 mmol) was dissolved in a methanol/water mixture (4:1, 10 ml). N,N-dimethylglycine (70 mg, 0.7 mmol) was added and the mixture was stirred for 12 h at 50° C. The solution was allowed to equilibrate to room temperature, concentrated and purified on a short C18 filter. A white crystalline solid was obtained. Yield: 20 mg (40%).

$^1$H NMR (500, DMSO-D6) δ 4.18 (s, 2H), 3.46 (s, 3H), 3.15 (s, 3H)

Anal. Calcd for C$_{21}$H$_{24}$N$_3$O$_{15}$Re$_3$ (trimer): C, 22.58; H, 2.17; N, 3.76. Found: C, 23.19; H, 2.78; N, 3.84

IR (KBr, cm$^{-1}$): 2022, 1911, 1890, 1866

MS (ESI+, MeOH) m/z: 1117.0 ([M]+) (trimer)

Synthesis of Compound (b1)

A solution of vitamin $B_{12}$ (100 mg, 73.8 mmol) and 1 (50 mg, 0.125 mmol) in 10 ml of methanol was stirred at room temperature over night. The reaction was controlled by HPLC measurements (solvent system 1, gradient 2). When no vitamin $B_{12}$ was detectable anymore, the solvent was evaporated, the crude product redissolved in water and filtered over a 0.2 μm filter to remove excess of 1. The filtrate was subjected to preparative HPLC purification (solvent system 1, gradient 2, 30 ml/min flow). The two isomers were separated from each other. The isomers were obtained as red powder in similar amounts ~(1:1). Total yield: 96%. For full characterisation see crystallographic data. Crystals of b1(b) were obtained by vapor diffusion of acetone into an aqueous solution of b1(b).

$^{31}$P NMR (81, CD$_3$OD) δ 0.68

IR (KBr, cm$^{-1}$): 3400, 2926, 2179, 2023, 1900, 1667, 1627, 1572, 1401, 1366, 1213, 1056

MS (ESI+, MeOH) m/z: 1737 (M+1)$^+$, 869 (M+2)$^{2+}$

CV: $E_{1/2}$=−652 mV vs. Ag+/AgCl, ca. 90% reversible

Synthesis of Compound (b2)

A solution of vitamin $B_{12}$ (50 mg, 36.9 mmol) and 2 (19.8 mg, 0.074 mmol) in 3 ml of methanol was stirred at room temperature for 48 hrs. The reaction was controlled by HPLC measurements (solvent system 1, gradient 2). When no vitamin $B_{12}$ was detectable anymore, the solvent was evaporated and the crude product subjected to preparative HPLC purification (solvent system 1, gradient 2, 30 ml/min flow). The isomers were obtained separately as red powder in similar amounts ~(1:1). Total yield: 76%

$^1$H NMR (500, D$_2$O) δ 0.43 (s, 3H, C20), 0.95-0.98 (m, 1H, C41'), 0.99 (s, 3H, C46), 1.08 (s, 3H, C54), 1.17-1.20 (m, 1H, C60'), 1.23 (d, 3H, Pr3, J=6.3 Hz), 1.42 (s, 3H, C36), 1.44 (s, 3H, C47), 1.65-1.80 (m, 2H, C42', C48'), 1.83 (s, 3H, C25), 1.88-2.10 (m, 6H, C30, C37, C41, C42, C48), 2.25 (s, 3H, B10), 2.28 (s, 3H, B11), 2.37-2.38 (m, 2H, C26), 2.41 (s, 3H, C53), 2.45-2.53 (m, 6H, C31, C49, C55), 2.56 (s, 3H, C35), 2.58-2.65 (m, 3H, C56, C60), 2.75-2.81 (m, 3H, C18, C37, Pr1'), 3.15 (d, 1H, C13, J=9.9 Hz), 3.63 (d, 1H, Pr1, J=13.7 Hz), 3.70 (dd, 1H, R5', J=12.6 and 4.2 Hz), 3.78 (d, 1H, C19, J=11.4 Hz), 3.86-3.90 (m, 2H, C8, R5), 4.00-4.02 (m, 1H, R4), 4.15 (t, 1H, R2, J=4.2 and 4.1 Hz), 4.26-4.33 (m, 1H, Pr2), 4.39 (d, 1H, C3, J=8.6 Hz), 4.63 (dt, 1H, R3, J=8.5 and 4.3, 4.0 and 3.6 Hz), 6.08 (s, 1H, C10), 6.23 (d, 1H, R1, J=3.0 Hz), 6.51 (s, 1H, B4), 7.02 (s, 1H, B2), 7.24 (s, 1H, B7), 8.13 (dd, 1H, L3, J=5.4 and 1.7 Hz), 8.51 (s, 1H, L1), 8.71. (d, 1H, L2, J=5.4 Hz)

$^{13}$C NMR (125, D$_2$O) δ 15.8, 16.5, 17.5, 18.4, 19.7, 19.9, 20.3, 20.4, 20.9, 21.1, 27.6, 27.7, 29.5, 32.4 (3C), 33.1 (2C), 33.7, 35.2, 36.3, 40.2, 42.8, 43.9, 46.9, 48.2-52.6 (2C below the solvent signal), 52.6, 55.3, 55.8, 58.4, 60.6, 62.7, 70.8, 73.7, 75.5, 76.9, 83.9, 86.7, 88.3, 96.1, 105.1, 108.1, 112.9, 117.6, 128.0, 129.6, 131.5, 134.3, 136.1, 138.0; 143.3, 152.0, 154.4, 166.4, 167.1, 168.0, 174.2 (3C), 175.3 (2C), 176.6 (3C), 177.6 (2C), 178.2, 180.7, 182.5, 193.4, 196.3 (2C)

MS (ESI+, MeOH) m/z: 1793 (M+1)$^+$, 1116 (fragment)

IR (KBr, cm$^{-1}$): 3411, 2972, 2179, 2027, 1918, 1903, 1665, 1611, 1572, 1498, 1402, 1214, 1154, 1061, 571

Synthesis of Compound (b3) with M=$^{99m}$Tc 500 ml of a 10$^{-4}$ M PBS soln. of 3, pH 7.4 were mixed with 500 ml of a 0.01 M aqueous soln. of vitamin B$_{12}$ and stirred at 40° C. for 1.5 hrs. The reaction was followed by HPLC (solvent system 1, gradient 2). The reaction reached an equilibrium after a turnover of 60%.

Synthesis of Compound (b4)

Vitamin B$_{12}$ (50 mg, 0.04 mmol) was dissolved in methanol (10 ml). [Re (dmg) (CO)$_3$]$_3$ 4 (45 mg, 0.04 mmol) was added and the mixture was stirred at r.t. for 12 h. Two adducts (clearly distinguishable by HPLC) formed (yield 25% and 36%). These were isolated and purified by preparative HPLC (solvent system 3, gradient 7). Yield: 10 mg, 14% (adduct 1), 12 mg, 17% (adduct 2). Crystals of b4(b) suitable for x-ray analysis were obtained by vapour diffusion of acetone in a H$_2$O solution of the complex. For full characterization see crystallographic data.

Anal. Calcd for C$_{70}$H$_{96}$CoN$_{15}$O$_{19}$PRe: C, 48.66; H, 5.60; N, 12.16

Found: C, 48.42; H, 5.01; N, 12.04 (b4(b))

IR (KBr, cm$^{-1}$): 2033, 1928, 1904

MS (ESI+, MeOH) m/z: 1728.7 (M+1)$^+$

Synthesis of Compound (b5)

A mixture of cis-diamminedichloroplatinum(II) (5) (66.4 mg, 0.221 mmol) and silver nitrate (37.6 mg, 0.221 mmol) in water (6 ml) was stirred at 35° C. for 2 hours. The precipitation was removed by centrifugation and washed with water (4 ml). The solutions were added to cyanocobalamin (300 mg, 0.221 mmol), and the resulting solution was stirred at 50° C. for 16 hours. HPLC analysis exhibited full conversion of the cobalamin. The solvent was removed in vacuo, and the crude product was purified by preparative HPLC (solvent system 3, gradient 4). Lyophilization of the product fraction gave b5 as a red powder. Yield: 259.8 mg, 72.6%.

Crystals of b5 were obtained by vapour diffusion of acetone into a saturated aqueous solution of b5.

UV/Vis: λ/nm (log ε/mol l$^{-1}$cm$^{-1}$)=279.9 (4.1), 361.9 (4.4), 519.9 (3.8), 550.9 (3.8).

IR (KBr, cm$^{-1}$): ν$_{CN}$ (st) 2199

$^{195}$Pt NMR (107, CD$_3$OD) δ −2340

MALDI-ToF MS m/z: 1607 [M-Cl+Na]$^+$, 1591 [M-Cl—NH$_3$+Na]$^+$, 1571 [M-Cl-2NH$_3$+Na]$^+$

CV: E$_{1/2}$=−515 mV vs. Ag+/AgCl, ca. 50% reversible

Synthesis of Compound (b6)

A solution of b5 (37.4 mg, 23.1 μmol) and 9-methylguanine (6) (4.2 mg, 25 μmol) in water (2 ml) was stirred at 50° C. After 4 days, HPLC analysis showed almost complete conversion of the starting materials. The solvent was removed in vacuo, and the crude product was purified by preparative HPLC (solvent system 3, gradient 5). Lyophilization of the product fraction gave b6 as a red powder. Yield: 32.0 mg, 79%. Crystals of b6 were obtained by vapour diffusion of acetone into a saturated aqueous solution of b6.

$^{31}$P NMR (202, CD$_3$OD): δ 0.73

MALDI-ToF MS: 1736 [M-CH$_3$]$^+$, 1715 [M-NH$_3$—CH$_3$]$^+$

Synthesis of Compound (b7)

A solution of b5 (58.5 mg, 36.1 μmol) and 2'-deoxyguanosine (7) (11.6 mg, 43.3 μmol) in water (5 ml) was stirred at 30° C. After 4 days, HPLC analysis showed almost complete conversion of the starting materials. The solvent was removed in vacuo, and the crude product was purified by preparative HPLC (solvent system 3, gradient 6). Lyophilization of the product fraction gave b7 as a red powder. Yield: 45.3 mg, 67.7%.

UV/Vis: λ/nm (log ε/mol l$^{-1}$cm$^{-1}$)=278.0 (4.2), 361.9 (4.2), 521.0 (3.7), 546.0 (3.7).

$^{31}$P NMR (202, CD$_3$OD): δ 0.71 (94%), 0.21 (6%)

$^{195}$Pt NMR (107, CD$_3$OD): δ −2475 (line with ca. 1.5 kHz)

MALDI-ToF MS: 1723 [M-ribose-2NH$_3$+Na]$^+$.

Preparation of $^{99m}$Tc (VitB$_{12}$)(X)$_2$(CO)$_3$ [X=Cl, H$_2$O]

$^{99m}$Tc(H$_2$O)$_3$(CO)$_3$$^+$ is prepared by adding 1 ml (50 mCi, but the radioactivity concentration does not need to be 50 mCi/ml, it works with lower and with higher) $^{99m}$Tc-pertechnetate to an IsoLink™ vial and boiling the resulting solution for 20 minutes. The tricarbonyl reaction mixture is allowed to cool down and acidified to pH 3 with HCl 1N.

Then, a 10 mM aqueous solution of vitamin B$_{12}$ is prepared by dissolving 68.0 mg of the vitamin in 5 ml of oxygen-free Water for Injections. A mixture of 0.1 ml of the $^{99m}$Tc-tricarbonyl solution and 0.9 ml of the 10 mM vitamin B$_{12}$ solution is allowed to react at 100° C. for 30 minutes under nitrogen atmosphere.

Preparation of $^{186}$Re(VitB$_{12}$)(X)$_2$(CO)$_3$ [X=Cl, H$_2$O]

A previously acidified (pH 2.5) solution of Re-186-perrhenate is added to a vial, sealed under nitrogen atmosphere, which contains a mixture of NH$_3$BH$_3$ and ascorbic acid. The reaction is completed after 10 minutes at room temperature. This is called a pre-reduction step.

A 10 mM aqueous solution of vitamin B$_{12}$ is prepared by dissolving 68.0 mg of the vitamin B$_{12}$ in 5 ml of oxygen-free Water for Injections. From the reduced rhenium solution, 1 ml is added to an IsoLink™ vial and allowed to react for 15 minutes at 100° C. The resulting solution, containing $^{186}$Re(H$_2$O)$_3$(CO)$_3$$^+$, is cooled down.

A mixture of 0.1 ml of the Rhenium tricarbonyl solution and 0.9 ml of the Vitamin B12 10 mM solution is kept at 100° C. for 45 min.

Figure 3:
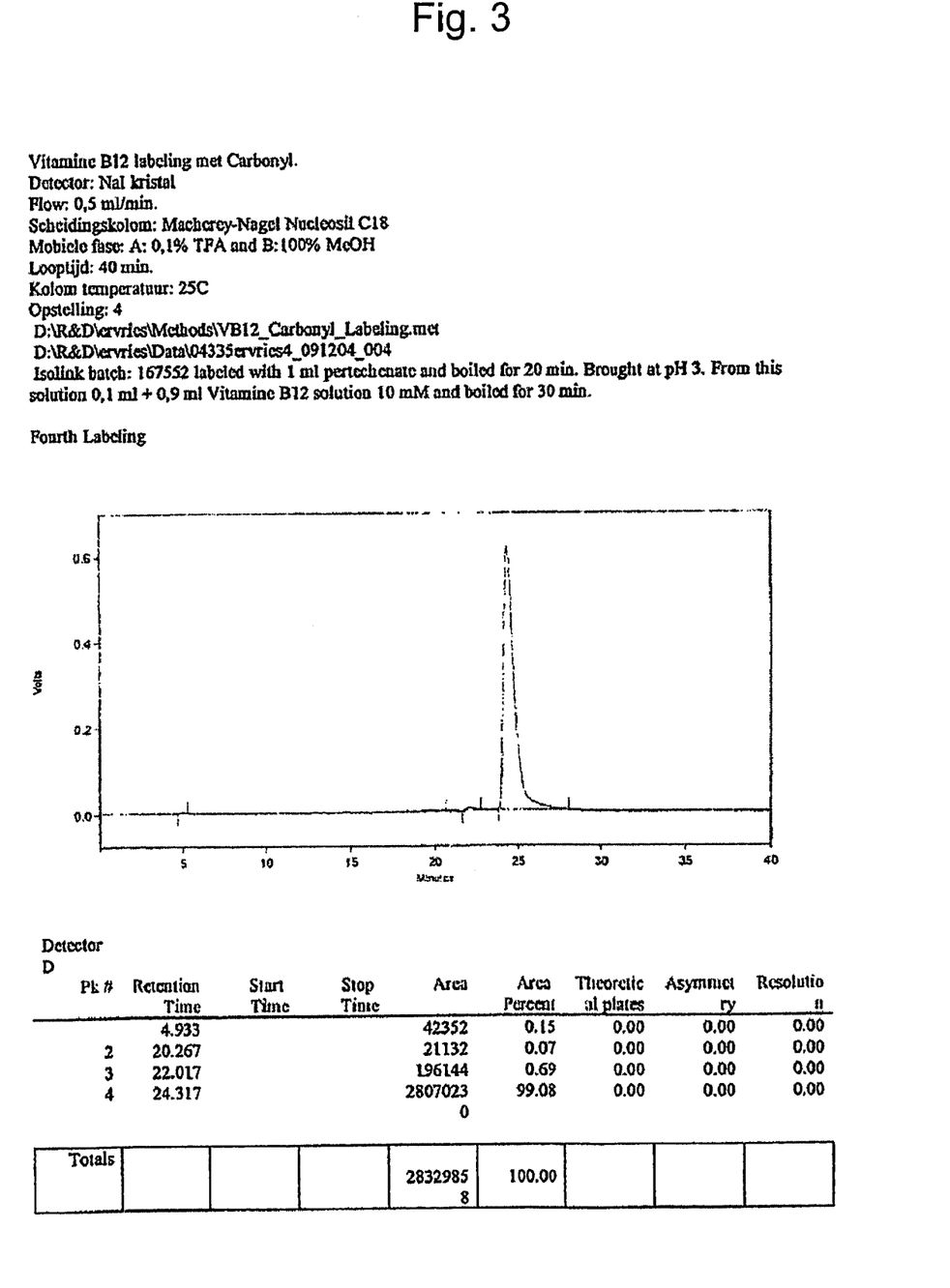
FIG. 3 shows an HPLC chromatogram of $^{99m}Tc(VitB_{12})(H_2O)(CO)_3$.
Figure 4:
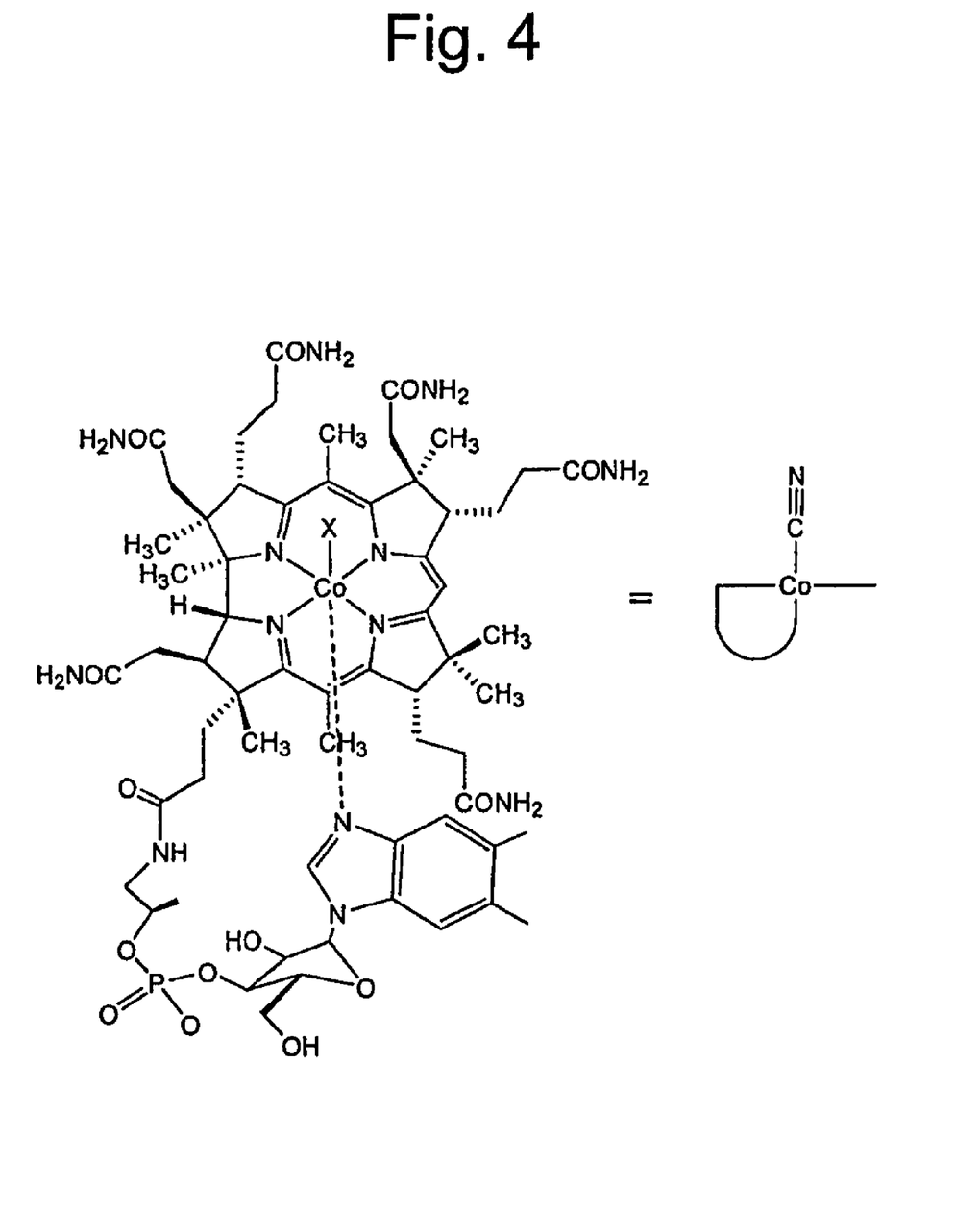
FIG. 4 shows the structural formula of vitamin $B_{12}$.
Figure 5A:
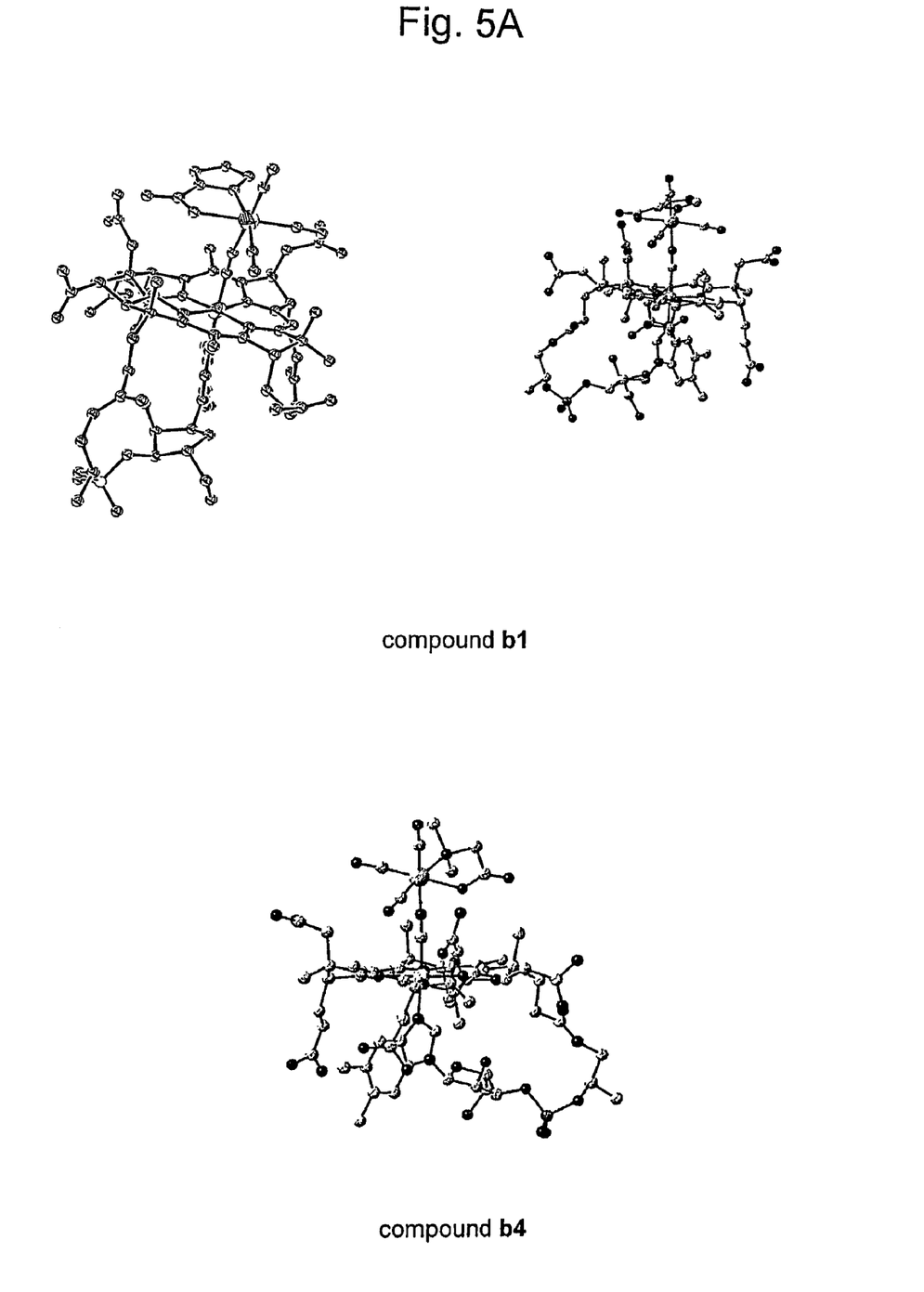
FIG. 5 shows X-ray structures of compounds b1, b4, b5 and b6.
Figure 5B:
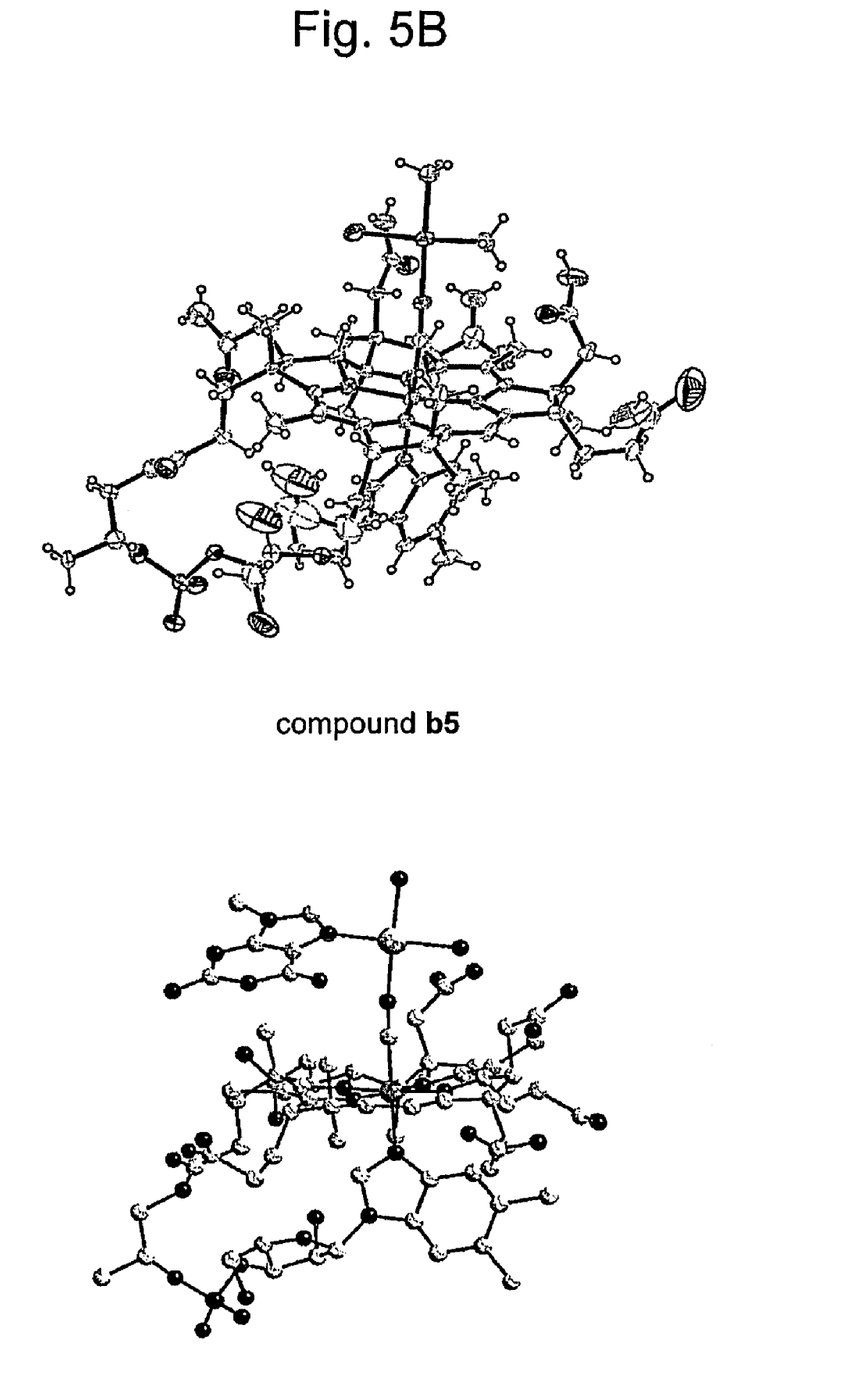

FIG. 3 is an example of an HPLC chromatogram of $^{99m}$Tc (Vit B$_{12}$)(H$_2$O)$_2$(CO)$_3$.

CRYSTALLOGRAPHIC DATA

X-Ray Table of Compound b1(b)

| | |
|---|---|
| Empirical formula | C70 H106 Co N16 O28 P Re |
| Formula weight | 1895.81 |
| Temperature | 183(2) K |
| Wavelength | 0.71073 Å |
| Crystal system | Orthorhombic |
| Space group | P212121 |
| Unit cell dimensions | a = 15.9578(10) Å α = 90°. |
| | b = 21.2328(12) Å β = 90°. |
| | c = 27.9776(13) Å γ = 90°. |
| Volume | 9479.6(9) Å3 |
| Z | 4 |
| Density (calculated) | 1.328 Mg/m$^3$ |
| Absorption coefficient | 1.545 mm$^{-1}$ |
| F(000) | 3916 |
| Crystal size | 0.57 × 0.15 × 0.04 mm$^3$ |
| Crystal description | red plate |
| Theta range for data collection | 2.16 to 25.00°. |
| Index ranges | −18 <= h <= 18, 0 <= k <= 25, |
| | 0 <= l <= 32 |
| Reflections collected | 16557 |
| Independent reflections | 16557 [R(int) = 0.0000] |
| Reflections observed | 10604 |
| Criterion for observation | >2sigma(I) |
| Completeness to theta = 25.00° | 98.8% |
| Absorption correction | Numerical |
| Max. and min. transmission | 0.9331 and 0.5508 |
| Refinement method | Full-matrix least-squares on F$^2$ |
| Data/restraints/parameters | 16557/40/1026 |
| Goodness-of-fit on F2 | 0.954 |
| Final R indices [I > 2sigma(I)] | R1 = 0.0990, wR2 = 0.2370 |
| R indices (all data) | R1 = 0.1297, wR2 = 0.2549 |
| Absolute structure parameter | −0.007(11) |
| Largest diff. peak and hole | 1.975 and −0.854 e.Å$^{-3}$ |

X-Ray Table of Compound b4(b)

| | |
|---|---|
| Empirical formula | C73 H112.60 Co N15 O27.30 P Re |
| Formula weight | 1913.28 |
| Temperature | 183(2) K |
| Wavelength | 0.71073 Å |
| Crystal system | Orthorhombic |
| Space group | P212121 |
| Unit cell dimensions | a = 15.8758(7) Å α = 90°. |
| | b = 21.8451(10) Å β = 90°. |
| | c = 26.3673(14) Å γ = 90°. |
| Volume | 9144.4(8) Å$^3$ |
| Z | 4 |
| Density (calculated) | 1.390 Mg/m$^3$ |
| Absorption coefficient | 1.601 mm$^{-1}$ |
| F(000) | 3964 |
| Crystal size | 0.46 × 0.08 × 0.07 mm$^3$ |
| Theta range for data collection | 1.86 to 26.00°. |
| Index ranges | −19 <= h <= 19, −26 <= k <= 26, |
| | −32 <= l <= 32 |
| Reflections collected | 68628 |
| Independent reflections | 17853 [R(int) = 0.1048] |
| Completeness to theta = 26.00° | 99.5% |
| Absorption correction | Numerical |
| Max. and min. transmission | 0.9257 and 0.7060 |
| Refinement method | Full-matrix least-squares on F$^2$ |
| Data/restraints/parameters | 17853/2/1071 |
| Goodness-of-fit on F2 | 0.900 |
| Final R indices [I > 2sigma(I)] | R1 = 0.0662, wR2 = 0.1588 |
| R indices (all data) | R1 = 0.1159, wR2 = 0.1742 |
| Absolute structure parameter | −0.014(8) |
| Largest diff. peak and hole | 2.044 and −1.063 e.Å$^{-3}$ |

X-Ray Data and Structure Refinement of Compounds b5

| | |
|---|---|
| Empirical formula | C$_{137}$H$_{184}$C$_{12}$Co$_2$F$_3$N$_{32}$O$_{56}$P$_2$Pt$_2$ |
| Formula weight | 3873.04 |
| Temperature | 183(2) K |
| Wavelength | 0.71073 Å |
| Crystal system | P1 |
| Space group | Triclinic |
| Unit cell dimensions | a = 16.9434(17) Å, |
| | α = 111.999(10)°. |
| | b = 17.3115(15) Å, |
| | β = 99.721(11)°. |
| | c = 18.0814(17) Å, |
| | γ = 90.580(11)°. |
| Volume | 4831.2(8) Å$^3$ |
| Z | 1 |
| Density (calculated) | 1.331 Mg/m$^3$ |
| Absorption coefficient | 1.741 mm − 1 |
| F(000) | 1979 |
| Crystal size | 0.34 × 0.14 × 0.10 mm$^3$ |
| Theta range for data collection | 2.31 to 28.05°. |
| Index ranges | −22 <= h <= 22, −22 <= k <= 22, |
| | −23 <= l <= 23 |
| Reflections collected | 46915 |
| Independent reflections | 38480 [R(int) = 0.0685] |
| Completeness to theta = 28.05° | 92.0% |
| Max. and min. transmission | 0.8545 and 0.7101 |
| Refinement method | Full-matrix least-squares on F$^2$ |
| Data/restraints/parameters | 38480/61/1937 |
| Goodness-of-fit on F2 | 0.914 |
| Final R indices [I > 2sigma(I)] | R1 = 0.0720, wR2 = 0.1731 |
| R indices (all data) | R1 = 0.1138, wR2 = 0.1925 |
| Absolute structure parameter | −0.015(5) |
| Largest diff. peak and hole | 1.141 and −1.967 e.Å$^{-3}$ |

REFERENCES

[1] 2.87 ed., STOE & Cie, GmbH, Darmstadt, Germany, 1998.

[2] G. M. Sheldrick, Acta Cryst. 1990, A46, 467.

[3] A. Altomare, M. C. Burla, M. Camalli, G. L. Cascarano, C. Giacovazzo, A. Guagliardi, A. G. G. Moliterni, G. Polidori, R. Spagna, J. Appl. Cryst. 1999, 32, 115.

[4] G. M. Sheldrick, University Göttingen, 1997.

[5] R. Alberto, A. Egli, U. Abram, K. Hegetschweiler, P. A. Schubiger, J. Chem. Soc. Dalton Trans. 1994, 2815.

[6] R. Alberto, K. Ortner, N. Wheatley, R. Schibli, A. P. Schubiger, J. Am. Chem. Soc. 2001, 123, 3135.

The invention claimed is:

1. Metal complex of the general formula M(L)$_n$, wherein M is metal selected from the transition metals, each L is independently selected and represents a ligand, at least one L is vitamin B$_{12}$ (cyanocobalamin) or a derivative thereof which is bound through the nitrogen atom of its cyanide group to M, thus, forming a M-NC-[Co] moiety, wherein [Co] represents vitamin B$_{12}$ or its derivative without cyanide, and wherein n is 1, 2, 3, 4, 5 or 6.

2. Metal complex as claimed in claim 1, wherein M is technetium, ruthenium, rhodium, rhenium, palladium, platinum, iridium or copper.

3. Metal complex as claimed in claim 1, wherein M is a radioisotope of rhenium or technetium.

4. Metal complex as claimed in claim 1, wherein n is 4, 5 or 6 and three occurrences of L are carbonyl groups (COs).

5. Metal complex as claimed in claim 4, wherein an occurrence of L is a bidentate ligand.

6. Metal complex as claimed in claim 5, wherein the bidentate ligand is selected from α-amino acids or derivatives of picolinic acid.

7. Metal complex as claimed in claim 1, wherein M is platinum, and L is independently selected from ligands containing N, S, P, O, C as the metal binding atom or any other donor with one non-binding electron pair available for coordination to the metal.

8. Metal complex as claimed in claim 4, wherein an occurrence of L is a bidentate ligand coupled to a molecule selected from the group consisting of fluorescing agents, optical dyes, NIR dyes, phosphorescent dyes, and pharmacophores.

9. Metal complex as claimed in claim 8, wherein the bidentate ligand is coupled to a fluorescing agent selected from the group consisting of fluoresceine, pyrene, acridine, and dansyl.

10. Metal complex as claimed in claim 8, wherein the bidentate ligand is coupled to a pharmacophores selected from the group consisting of tamoxifen, methotrexate and cyclophosphamid.

11. Process for preparing a metal complex, comprising:
mixing vitamin $B_{12}$ or a derivative thereof with a precursor complex of the general formula $M(L)_{n-1}L'$, wherein M is a transition metal, n is 2, 3, 4, 5 or 6, L' is a ligand to be substituted by the vitamin $B_{12}$ or the derivative thereof, and each L is independently selected and is a ligand.

12. Precursor complex for use in the preparation of metal complex of claim 1 and being selected from the group consisting of:

wherein M is a transition metal, and one of the ligands attached thereto is capable of being substituted by vitamin $B_{12}$.

13. A method for using a metal complex of claim 1 in radiodiagnostics, chemotherapy or radionuclide therapy comprising the step of administering the metal complex of claim 1 to a host in need of such diagnostics or therapy.

14. Metal complex as claimed in claim 1, wherein M is a catalytically active metal.

15. Metal complex as claimed in claim 3, wherein M is $^{99m}Tc$, $^{188}Re$, or $^{186}Re$.

16. Metal complex as claimed in claim 5, wherein the bidentate ligand comprises two aliphatic and aromatic amine parts, two aliphatic or aromatic amine parts, or one aliphatic or aromatic amine part and an anionic group.

17. Metal complex as claimed in claim 4, wherein an occurrence of L is a bidentate ligand coupled to a metal complex, a biologically active molecule or a fluorescing agent.

18. Metal complex as claimed in claim 16, wherein the bidentate ligand comprises one aliphatic or aromatic amine part and an anionic group, wherein the anionic group is a carboxylate, a thiolate or a hydroxylate.

19. Metal complex as claimed in claim 1, wherein M is platinum, L is independently selected from:
ligands containing N, S, P, O, C as the metal binding atom or any other donor with one non-binding electron pair available for coordination to the metal; and
ligands containing N, S, P, O, C as the metal binding atom or any other donor with one non-binding electron pair available for coordination to the metal coupled to another metal complex, a biologically active molecule, or a fluorescing molecule.

20. Metal complex as claimed in claim 1 having a structural formula selected from the group consisting of:

-continued

21. The process of claim 11 wherein the precursor complex is cis-diamminedichloroplatinum(II).

22. Precursor complex as claimed in claim 12, wherein M is technetium, rhodium, rhenium, palladium, or platinum.

23. Metal complex as claimed in claim 1, wherein M is technetium, rhodium, rhenium, palladium, or platinum.

* * * * *